United States Patent [19]
Andersen et al.

[11] Patent Number: 5,439,444
[45] Date of Patent: * Aug. 8, 1995

[54] PRE-FORMED MEMBER FOR PERCUTANEOUS CATHETER

[75] Inventors: Erik Andersen, Gurnee; David G. Quinn, Grayslake, both of Ill.

[73] Assignee: Corpak, Inc., Wheeling, Ill.

[ * ] Notice: The portion of the term of this patent subsequent to May 3, 2011 has been disclaimed.

[21] Appl. No.: 233,447

[22] Filed: Apr. 26, 1994

Related U.S. Application Data

[63] Continuation-in-part of Ser. No. 646,889, Jan. 28, 1991, Pat. No. 5,308,325.

[51] Int. Cl.$^6$ ............................................. A61M 29/00
[52] U.S. Cl. ..................................... 604/96; 604/174; 604/175; 156/60; 156/73.1
[58] Field of Search ........................... 604/93, 96–104, 604/30, 34, 167, 174, 256, 277, 278, 246, 247, 264; 156/580.1, 60, 73.1, 73.2; 600/29, 31; 128/768, 766; 606/192–194

[56] References Cited

U.S. PATENT DOCUMENTS

| | | |
|---|---|---|
| 3,640,282 | 2/1972 | Kamen et al. . |
| 3,799,173 | 3/1974 | Kamen . |
| 3,831,587 | 8/1974 | Boyd . |
| 3,889,685 | 6/1975 | Miller, Jr. et al. . |
| 4,057,065 | 11/1977 | Thow . |
| 4,114,625 | 9/1978 | Onat . |
| 4,148,319 | 4/1979 | Kasper et al. . |
| 4,344,434 | 8/1982 | Robertson . |
| 4,364,394 | 12/1982 | Wilkinson . |
| 4,531,943 | 7/1985 | Van Tassel et al. . |
| 4,543,089 | 9/1985 | Moss . |
| 4,574,173 | 3/1986 | Bennett . |
| 4,685,901 | 8/1987 | Parks . |
| 4,779,611 | 10/1988 | Grooters et al. . |
| 4,811,737 | 3/1989 | Rydell . |
| 4,820,270 | 4/1989 | Hardcastle et al. . |
| 4,822,338 | 4/1989 | Longmore et al. . |
| 4,900,306 | 2/1990 | Quinn et al. . |
| 4,943,275 | 7/1990 | Stricker . |
| 4,946,440 | 8/1990 | Hall . |
| 4,990,139 | 2/1991 | Jang . |
| 5,059,178 | 10/1991 | Ya . |
| 5,078,681 | 1/1992 | Kawashima . |
| 5,308,325 | 5/1994 | Quinn et al. . |

FOREIGN PATENT DOCUMENTS 1380991 1/1975 United Kingdom .

Primary Examiner—C. Fred Rosenbaum
Assistant Examiner—Mark Bockelman
Attorney, Agent, or Firm—Wallenstein & Wagner, Ltd.

[57] ABSTRACT

The present invention is directed to a pre-formed retention member having an improved construction and used for anchoring or retaining a catheter within a body cavity, organ or vessel. The pre-formed retention retains a distal open end of a single body access tube against an inner body cavity wall of a patient. The pre-formed member is secured to only the inner and outer peripheral edges of the distal open end of the tube by a sleeve. The sleeve has both an outer sleeve surface and an inner sleeve surface which receives, respectively, the outer and inner surfaces of the tube. The pre-formed member includes an outer surface and an inner surface which defines a retention chamber. The retention chamber extends beyond the distal open end of the tube so that no portion of the tube passes through the chamber. When outside forces act upon the pre-formed member, the pre-formed member collapses upon itself, and in a collapsed configuration, the outer diameter of the pre-formed member is no greater than the outer diameter of the tube.

8 Claims, 3 Drawing Sheets

FIG. 5
FIG. 6
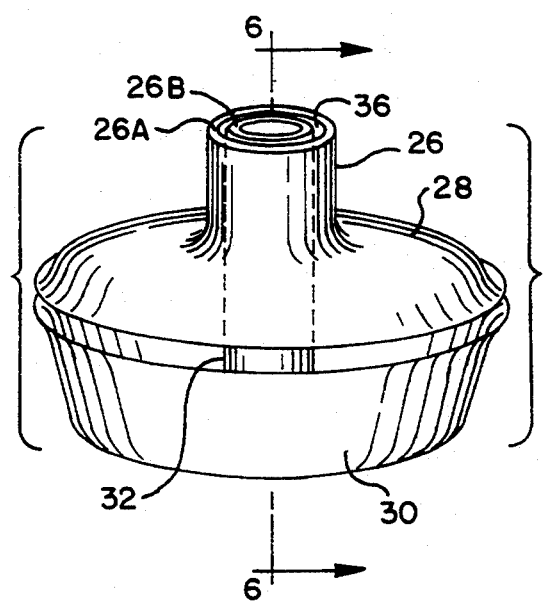
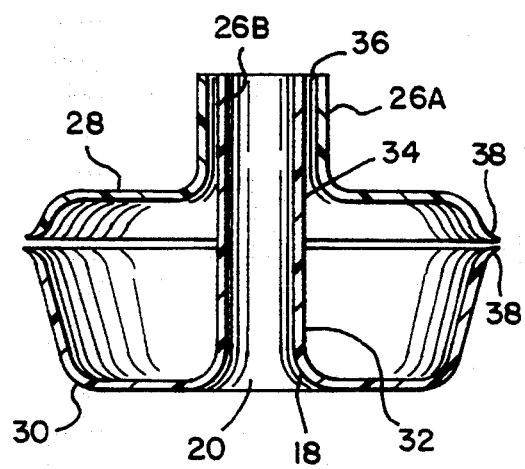
FIG. 7
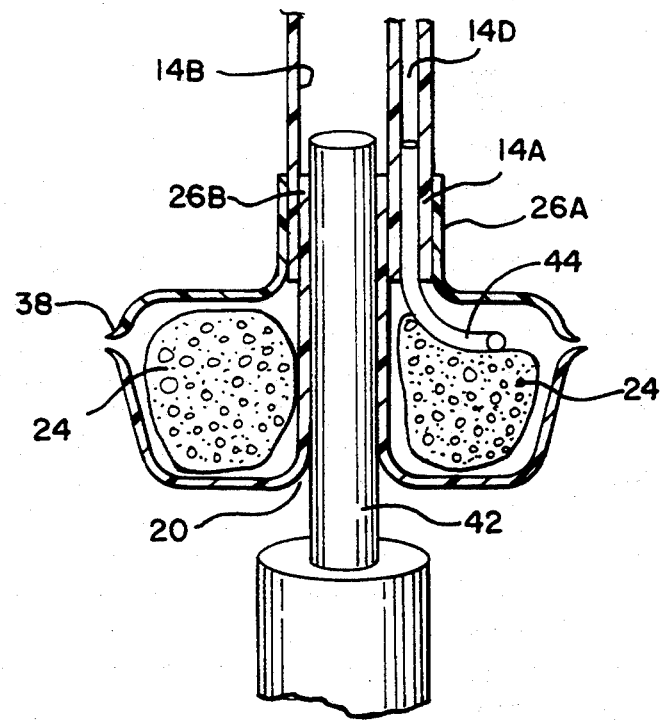

PRE-FORMED MEMBER FOR PERCUTANEOUS CATHETER

RELATED APPLICATION

The present application is a continuation-in-part of U.S. application Ser. No. 07/646,889, filed on Jan. 28, 1991, to issue as U.S. Pat. No. 5,308,325 on May 3, 1994.

TECHNICAL FIELD

The present invention generally relates to catheters for placement within body vessels, cavities or organs, such as catheters used in angioplasty, gastrostomy, cystostomy or jejunostomy procedures. Specifically, the invention relates to a pre-formed member for anchoring or retaining a catheter within a body cavity, organ or vessel.

BACKGROUND OF THE INVENTION

The use of compressible and expandable retention members, such as those utilizing balloons or cuffs, are well known in a wide variety of medical fields. For example, U.S. Pat. Nos. 3,640,282 and 3,799,173 disclose expandable and compressible foam-filled retention cuffs used on endotracheal tubes. U.S. Pat. Nos. 4,795,430 and 4,900,306 disclose the use of inflatable and compressible foam-filled retention balloons in percutaneous endoscopic gastrostomy tubes. Inflatable balloons carried on catheters also find clinical applications in angioplasty.

FIGS. 1 and 2 disclose a prior art retention member a in a fully expanded configuration. FIG. 1A discloses the same retention member in a fully collapsed configuration. The retention member may be an annular-shaped balloon member secured near a distal open end b of a percutaneous catheter, such as a gastrostomy tube c having a fluid lumen d. Typically, the retention member a is circumferentially secured solely to the outer surface of the tube c.

The retention member a may be expandable through a secondary lumen e, typically an air lumen. Further, an expansion chamber f of the retention member a may be substantially filled with a polyurethane foam g to urge retention member a to assume the expanded outer configuration. Foam g, however, is sufficiently compressible to permit the retention member a to assume the collapsed or deformed outer configuration shown in FIG. 1A.

One disadvantage of the structure of retention member a occurs upon collapse. As shown in FIG. 1A, because retention member a is circumferentially secured to the outer surface of tube c, upon collapse, the retention member a collapses around the outer diameter of the tube. As a result, the overall outer dimensions of the collapsed retention member a exceeds the outer diameter of the tube. This causes extraction and removal of the retention member a through the stoma to be more difficult and increases the risk of damage to the exit site of the stoma.

Hence, prior to the development of the present invention, a need existed for a pre-formed retention member capable of being in a collapsed state and used for percutaneous tubes and other internally anchored catheters which would overcome these and other problems.

SUMMARY OF THE INVENTION

According to the present invention, an improved construction has been developed for a pre-formed member for percutaneous catheters and other catheters anchored or retained within a body cavity or organ. The pre-formed member is constructed in such a way that it has an expanded form in its normal, original shape. The shape of the pre-formed member may be expanded further when the pre-formed member is substantially filled with a compressible foam. When the pre-formed member is inserted into a body cavity or opening of a patient, outside forces, such as pressure from the wall of the body cavity or opening against the pre-formed member, cause the pre-formed member to deform or collapse temporarily. In a collapsed state, the pre-formed retention member of the present invention collapses upon itself rather than on the outer surface of the tube. This achieves an outer configuration no greater than the outer diameter of the tube itself.

Generally, the pre-formed member of the present invention is annular in shape or donut shaped when it is in a substantially expanded form. Such annular shape retains a distal open end of the tube against an inner body cavity wall of the patient. This maintains the tube securely within the body cavity and prevents its inadvertent extraction through the surgically formed stoma. Unlike the previous retention devices and balloons discussed above, the pre-formed member of the present invention is secured to only the inner and outer peripheral edges of the distal open end of the tube. Specifically, the pre-formed member of the present invention is adhered to both outer and inner surfaces of the peripheral edge of the distal end of the tube by means of a sleeve. The sleeve has both an outer sleeve surface and an inner sleeve surface which receives or corresponds to, respectively, the outer tube surface and the inner tube surface of the tube.

The pre-formed member includes an outer member surface and an inner member surface which defines retention chambers. Unlike the retention members and balloons discussed above, the retention chambers extend beyond the distal open end of the tube so that no portion of the tube passes through the chamber. Instead, fluid flow through the fluid lumen of the tube passes through an axial opening in the pre-formed member to permit passage of fluid out of the tube.

Another beneficial result of the construction of the pre-formed member of the present invention occurs upon collapse of the pre-formed member. Again, because the retention chambers extend beyond the distal open end of the tube, upon collapse of the pre-formed member, the pre-formed member collapses upon itself rather than around the outer surface of the tube. As a result, the outer dimensions of the collapsed pre-formed member approximates the outer diameter of the tube.

Unlike the retention devices discussed above, which are directed to balloons which may be inflated or deflated, the pre-formed member of the present invention is constructed in its relaxed, original form. In order to retain or regain its original form after its collapse, the pre-formed member may contain compressible foam in the retention chamber.

Other advantages and aspects of the invention will become apparent upon making reference to the specification, claims, and drawings to follow.

BRIEF DESCRIPTION OF DRAWINGS

FIG. 5 is an exploded view of a preferred embodiment of the present invention;

FIG. 6 is a vertical section taken along line 6—6 of FIG. 5; and,

FIG. 7 discloses a preferred manufacturing method for the present invention.

DETAILED DESCRIPTION

Figure 2A:
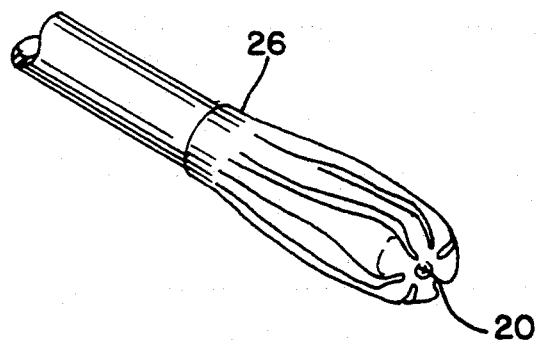
FIG. 2A is a pre-formed member of the present invention in a fully collapsed state.

While this invention is susceptible of embodiment in many different forms, there is shown in the drawings and will herein be described in detail a preferred embodiment of the invention. The present disclosure is to be considered as an exemplification of the principles of the invention and is not intended to limit the broad aspect of the invention to the embodiment illustrated.

Specifically, while the present invention is exemplified with reference to a percutaneous catheter, the present invention finds application for any catheter which may be used with a pre-formed member within a body cavity, organ or vessel.

Figure 3:
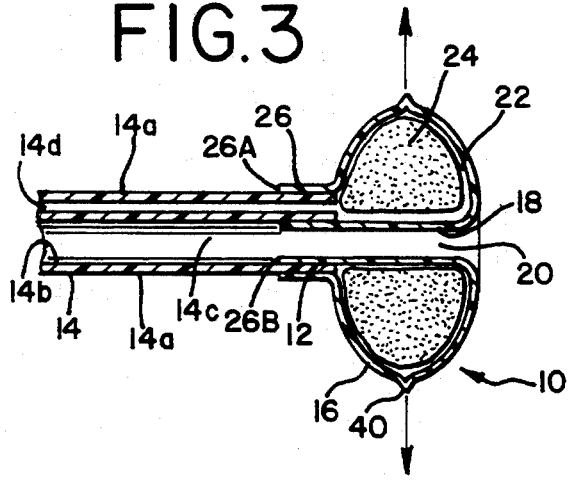
FIG. 3 is a vertical section taken through one embodiment of the present invention shown in a fully expanded state.

Referring now to the drawings, FIG. 3 generally discloses an improved retention member, preferably a pre-formed member 10, made in accordance with the present invention. The pre-formed member 10 is preferably made from a medical grade polyurethane plastic. The pre-formed member is constructed in such a way that it has an expanded form in its normal, original configuration. By pre-forming the pre-formed member 10 with a substantially fixed outer configuration, the pre-formed member 10 is capable of repeatedly having and returning to a uniform outer configuration upon collapse and return to its original shape. This assures that when the pre-formed member 10 returns to its original form after collapse and within a body cavity of a patient, the pre-formed member 10 will assume a fully expanded state having an outer configuration of necessary size and proportion. The pre-formed member 10 may be assisted in returning to its original form with the aid of a compressible foam.

As disclosed in FIG. 3, the pre-formed member 10 is circumferentially secured to a distal open end 12 of a percutaneous single body access tube, such as a gastrostomy tube 14. The tube 14 has an outer tube surface 14A, an inner tube surface 14B and a fluid lumen 14C which accommodates fluid flow through the tube. The tube 14 also has an air lumen 14D which may aid in maintaining the expanded or collapsed configuration of the pre-formed member 10.

The pre-formed member 10 includes an outer member surface 16 which is generally coextensive with the outer tube surface 14A of the tube 14. The outer member surface 16 turns inwardly to define an inner member surface 18. The inner member surface 18 surrounds an axial opening 20 which is in fluid communication with the fluid lumen 14C of the tube 14. Hence, unlike prior art retention members or balloons, fluid within tube 14 passes through the pre-formed member 10 itself.

The outer member surface 16 and the inner member surface 18 of the pre-formed member 10 define a retention chamber 22 which may be substantially filled with a polyurethane, compressible foam 24. In this configuration, the foam 24 assists in returning the pre-formed member back to its original shape after insertion through the body cavity. However, the annular or donut configuration of the pre-formed member 10 lends itself to re-expansion of the pre-formed member without the presence of the foam 24. The chamber 22 may also be expanded manually via the use of a syringe containing fluid or air. To aid the pre-formed member 10 in its use as a retention device, air flowing into the retention chamber 22 from the air lumen 14D may be trapped in the chamber 22, so that the pre-formed member 10 is maintained in a substantially expanded form. The air may be trapped with the use of an inflation lumen plug or pin (not shown) which may be inserted into the end of the air lumen 14D. Unlike prior art retention members or balloons, the retention chamber 22 of the present invention extends beyond the distal open end 12 of the tube 14 so that no portion of the tube 14 passes through the chamber 22. This eliminates many of the disadvantages associated with the collapse and return to its original shape by the pre-formed member 10.

Figure 3A:
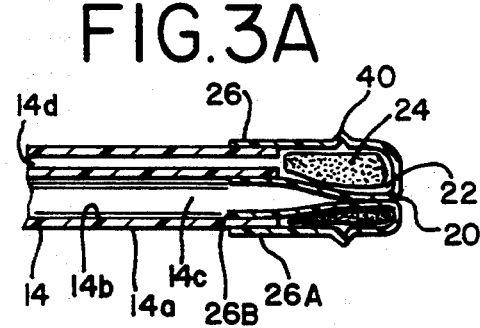
FIG. 3A is the same view as FIG. 3 disclosing the pre-formed member of the present invention in a fully collapsed state.

The pre-formed member 10 is secured to the open distal end 12 of the tube 14 by means of a sleeve 26 which preferably is integral with the pre-formed member 10. The sleeve 26 has an outer sleeve surface 26A and an inner sleeve surface 26B. The outer sleeve surface 26A and the inner sleeve surface 26B are secured to the respective outer tube surface 14A and inner tube surface 14B of the tube 14, as shown in FIGS. 3 and 3A. Preferably, the outer sleeve surface 26A and the inner sleeve surface 26B are RF welded in a manner to be described below in greater detail, or solvent bonded to the outer tube surface 14A and the inner tube surface 14B of the tube 14, using techniques well known in the art.

As a result of the foregoing described structure, the pre-formed member 10, when in a substantially expanded state, forms the axial opening 20, which has inner dimensions generally the same as the inner dimensions of the fluid lumen 14C. When the pre-formed member 10 is in a non-collapsed configuration, the pre-formed member 10 projects beyond the distal end 12 of the tube 14 and has an outer configuration with an outer diameter or dimensions greater than the outer diameter of the tube 14.

As best disclosed in FIGS. 2A and 3A, when in a fully collapsed state, the pre-formed member 10 assumes an outer collapsed configuration with an outer diameter no greater than the outer diameter of the tube 14. Because the retention chamber 22 extends beyond the open distal end 12 of the tube 14, due to release of pressure within the retention chamber 22 and due to the presence of outside pressure from the body cavity or stoma exit site, the pre-formed member 10 collapses upon itself during extraction through the stoma and the stoma exit site of the patient.

Figure 2B:
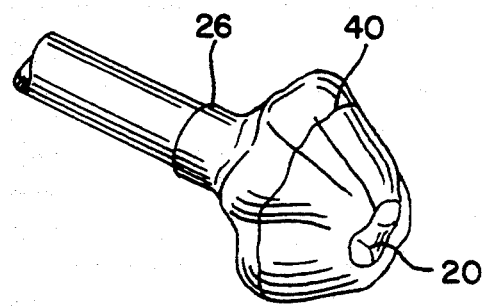
FIG. 2B is the same view as FIG. 2A disclosing the pre-formed member of the present invention in an intermediate collapsed state.
Figure 2C:
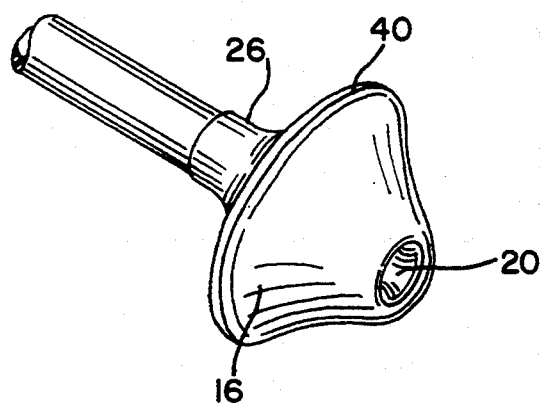
FIG. 2C is the same view as FIG. 2A disclosing the pre-formed member of the present invention in an intermediate expanded state.
Figure 2D:
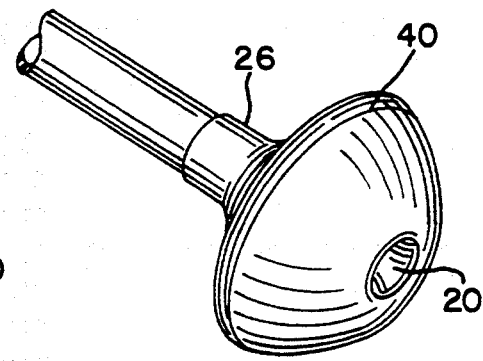
FIG. 2D is the same view as FIG. 2A disclosing the pre-formed member of the present invention in a fully expanded state.
Figure 1:
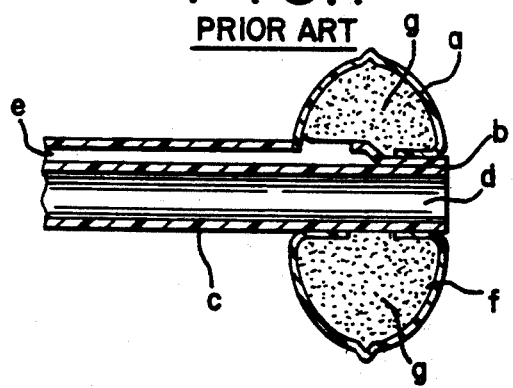
FIG. 1 is a vertical section taken through a prior art retention member or balloon in an expanded state.
Figure 1A:
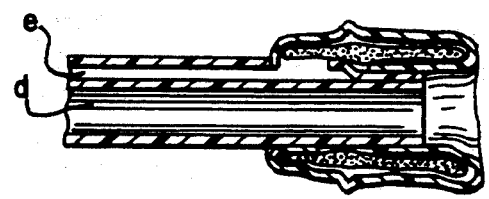
FIG. 1A is the same view as FIG. I disclosing the prior art retention member or balloon in a deflated state.

FIG. 2B discloses the pre-formed member 10 in a semi-collapsed state in which the axial opening 20 begins to form. In FIG. 2C, the outer member surface 16 of the pre-formed member 10 begins to assume the shape of the pre-formed expanded outer configuration, which shape is completely assumed as disclosed in FIG. 2D.

Figure 4A:
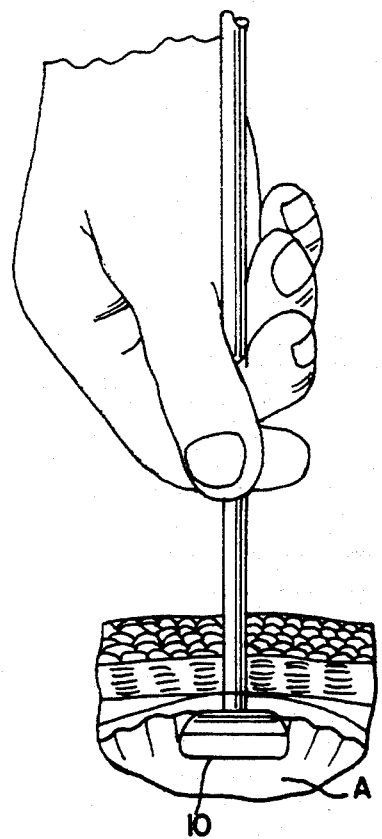
FIGS. 4A–4C disclose the steps of extraction of a percutaneous tube having a pre-formed member of the present invention carried on a distal open end thereof.
Figure 4B:
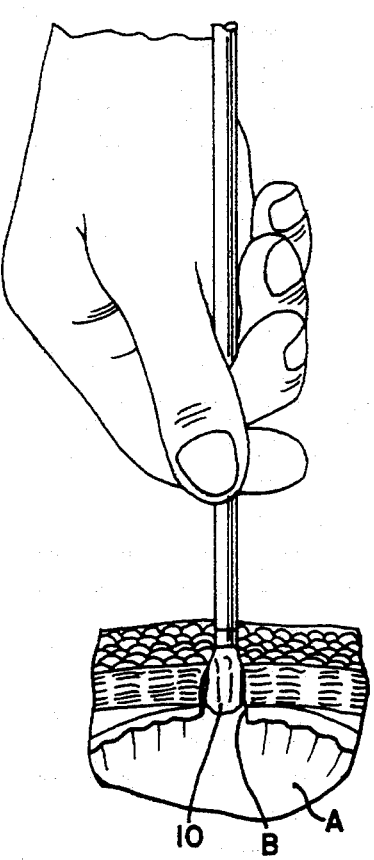
Figure 4C:
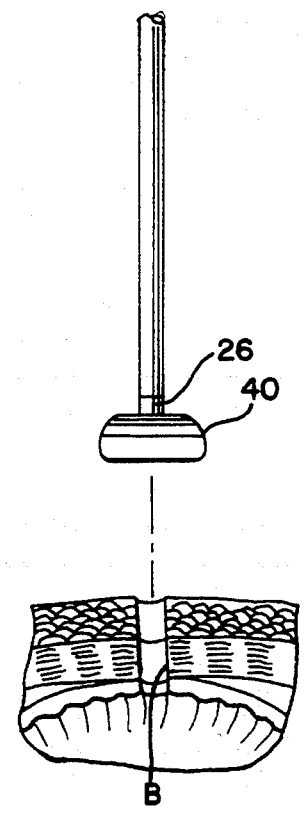

FIGS. 4A, 4B and 4C disclose a method of extracting the pre-formed member 10 from within a body cavity and through the stoma and stoma exit site of a patient. FIG. 4A disclose the pre-formed member 10 having a fully or substantially expanded outer configuration and anchored within a body cavity A. Due to the pliability of the outer member surface 16 of the pre-formed member 10, a health attendant can extract the pre-formed member 10 through a stoma B. In so doing, the outside forces, such as pressure, from the inner surfaces of stoma B urge the pre-formed member 10 into a collapsed state as shown in FIG. 4B. Upon full extraction of the pre-formed member 10, as disclosed in FIG. 4C, the pre-formed member 10 re-expands to its pre-formed shape and if used with compressible foam 24, the compressible foam within the chamber 22 springs back to its original shape. This is due to the absence of pressure from the inner walls of stoma B acting upon the pre-formed member 10.

FIGS. 5 through 7 disclose a preferred method of manufacturing the pre-formed member 10. As shown in FIGS. 5 and 6, the pre-formed member 10 is preferably formed from two molded elastomeric plastic parts, such as polyurethane or other elastomeric plastic parts. A proximal portion 28 defines a top half of the pre-formed member 10, and a distal portion 30 defines a bottom half of the pre-formed member 10. The sleeve 26 is preferably integrally formed as part of the proximal portion 28. This provides the sleeve 26 with an outer core to function as the outer sleeve surface 26A for securement to the outer tube surface 14A of the tube 14. Integrally formed in the distal portion 30 is an inner core 32 of which an upper portion 34 functions as the inner sleeve surface 26B for securement to the inner tube surface 14B of the tube 14. In the upper portion 34, the inner core 32 is inserted within the outer sleeve surface 26A to complete the overall construction of the sleeve 26. Defined between the outer sleeve surface 26A and the inner sleeve surface 26B is a circumferential gap 36 into which is inserted the open distal end 12 of the tube 14. The inner core 32 also defines the axial opening 20 to receive fluid from the fluid lumen 14C of the tube 14. Two circumferential peripheral edges 38 on the proximal portion 28 and the distal portion 30 are slightly flanged. This permits the formation of a perimeter seal about the circumference of the pre-formed member 10 at the completion of the manufacturing operation.

FIG. 7 discloses a preferred method of RF sealing of the sleeve 26 of the pre-formed member 10 to the distal end 12 of the tube 14. First, the proximal portion 28 is placed on the tube 14, such that the inner sleeve surface 26B contacts the outer tube surface 14A approximately ⅛ inch from the distal end 12 of the tube 14. Then, the inner core 32 of the distal tube portion 30 is placed approximately ⅛ inch inside the tube 14 through the distal end 12. This permits the inner tube surface 14B of the tube 14 to contact the inner sleeve surface 26B of the core 32 of the distal portion 30. A mandrel 44 is inserted into the air lumen 14D of the tube 14 and a mandrel 42 is inserted into the axial opening 20 until approximately 1/32 inch of the mandrel 42 extends beyond the interface of the inner sleeve surface 26B and the outer sleeve surface 26A of the sleeve 26 in the tube 14. Electronic welding or RF welding is then externally applied to seal and fuse the outer sleeve surface 26A to the outer tube surface 14A and the inner sleeve surface 26B to the inner tube surface 14B. During RF welding, the mandrel 42 prevents the fluid lumen 14C from closure while the mandrel 44 prevents similar closure of the air lumen 14D.

After RF welding has been completed, both the mandrels 42, 44 are removed. An annular or donut-shaped segment of the foam 24, having a central hole, is then placed within the pre-formed member 10. This is achieved by folding and deforming the distal pre-formed member portion 30 such that it can pass through the central hole in the annular foam segment 24.

Finally, the pre-formed member 10 is completed by RF sealing together the circumferential peripheral edges 38 on the proximal portion 28 and the distal portion 30, thereby forming a perimeter seal about the circumference of the pre-formed member 10.

While the specific embodiments have been illustrated and described, numerous modifications come to mind without significantly departing from the spirit of the invention and the scope of protection is only limited by the scope of the accompanying claims.

What is claimed is:

1. In a single body access tube having an inner tube surface and an outer tube surface defining a fluid lumen and an inflation lumen, the tube including a pre-formed retention member carried near a distal open end of the tube, the pre-formed member having a retention chamber surrounding the outer surface of the tube, the pre-formed member circumferentially secured to the outer surface of the tube, the improvement comprising:

the pre-formed member being circumferentially secured to the distal open end of the tube and to both the inner tube surface and the outer tube surface, the pre-formed member having an axial opening communicating with the fluid lumen of the tube, wherein the retention chamber of the pre-formed member is substantially filled with a compressible foam, and further wherein the retention chamber extends beyond the distal open end of the tube so that no portion of the tube passes through the chamber;

the pre-formed member being collapsible from its pre-formed configuration, and expandable to its non-collapsed, pre-formed configuration by passage of fluid flow through the inflation lumen, such that when the pre-formed member is in a non-collapsed, pre-formed configuration, the pre-formed member projects beyond the distal end of the tube and has an outer configuration with an outer diameter greater than the outer diameter of the tube, and such that when the pre-formed member is in a collapsed configuration, the pre-formed member collapses upon itself and has an outer collapsed configuration with an outer diameter no greater than the outer diameter of the tube.

2. The body access tube of claim 1 wherein a proximal end of the pre-formed member includes a sleeve, the sleeve having an outer sleeve surface and an inner sleeve surface for respective securement to the outer tube surface and the inner tube surface of the tube.

3. A percutaneous access device comprising:

a tube having an outer surface and an inner surface defining a fluid lumen and an inflation lumen;

the tube having a proximal end and a distal end;

a pre-formed retention member circumferentially secured to the distal end of the tube;

a passageway through the pre-formed retention member in fluid communication with the fluid lumen of the tube;

the pre-formed retention member having a retention chamber in fluid communication with the inflation lumen;

the retention chamber having a pre-formed configuration and being collapsible from its pre-formed configuration by passage of fluid flow through the inflation lumen;

the retention chamber, when in a non-collapsed configuration, projects beyond the distal end of the tube and has a configuration with an outer diameter greater than the outer diameter of the tube, and having at least one generally flattened surface perpendicular to the tube facing the proximal end of the tube;

the retention chamber, when in a collapsed configuration, projects beyond the distal end of the tube and has a configuration with an outer diameter approximately equal to or less than the outer diameter of the tube.

4. The device of claim 3 wherein the retention chamber is substantially filled with compressible foam.

5. The device of claim 4 wherein the foam is a polyurethane foam.

6. The device of claim 3 wherein the passageway through the pre-formed retention member is axially aligned with the fluid lumen of the tube.

7. A method of forming a pre-formed retention member carried on a distal open end of a catheter tube, the catheter having a fluid lumen and an inflation lumen, the method comprising the steps of:

forming a proximal portion of the pre-formed retention member, the proximal portion having a sleeve with a small diameter mating end to receive and contact an outer surface of the distal end of the catheter tube and the proximal portion having at least one generally flattened surface integral with said small diameter mating end and perpendicular to said catheter tube, and said proximal portion having a large diameter mating end;

forming a distal portion of the pre-formed member, the distal portion having a large diameter mating end for circumferentially mating with the large diameter mating end of the proximal portion, the distal portion having a core coaxial with the sleeve, the core being insertable within only the fluid lumen to contact an inner surface of the catheter;

inserting a fluid lumen mandrel into the core and fluid lumen;

inserting an inflation lumen mandrel into the inflation lumen;

bonding the sleeve to the outer surface of the catheter and the core to the inner surface of the catheter; and, circumferentially bonding together the large diameter mating ends of the proximal portion and the distal portion.

8. The method of claim 7 further including the step of substantially filling the pre-formed retention member with compressible foam material.

* * * * *